US006797472B1

(12) United States Patent
Liggett

(10) Patent No.: US 6,797,472 B1
(45) Date of Patent: Sep. 28, 2004

(54) VARIATION IN DRUG RESPONSE RELATED TO POLYMORPHISMS IN $\beta_2$-ADRENERGIC RECEPTOR

(75) Inventor: Stephen B. Liggett, Cincinnati, OH (US)

(73) Assignees: Genaissance Pharmaceuticals, Inc., New Haven, CT (US); University of Cincinnati, Cincinnati, OH (US)

(*) Notice: Subject to any disclaimer, the term of this patent is extended or adjusted under 35 U.S.C. 154(b) by 0 days.

(21) Appl. No.: 09/936,499

(22) PCT Filed: Mar. 10, 2000

(86) PCT No.: PCT/US00/06502

§ 371 (c)(1),
(2), (4) Date: Dec. 17, 2001

(87) PCT Pub. No.: WO01/06910

PCT Pub. Date: Feb. 1, 2001

Related U.S. Application Data

(60) Provisional application No. 60/124,060, filed on Mar. 12, 1999.

(51) Int. Cl.[7] ............................ C12Q 1/68; C07H 21/04
(52) U.S. Cl. ........................ 435/6; 435/91.1; 435/91.2; 536/23.1
(58) Field of Search .......................... 435/6, 91.2, 91.1; 536/23.1

(56) References Cited

U.S. PATENT DOCUMENTS 5,871,734 A * 2/1999 Lobb et al. ............... 424/144.1
6,156,503 A   12/2000 Drazen et al.

FOREIGN PATENT DOCUMENTS

WO    WO 00/31307 A1    6/2000

OTHER PUBLICATIONS

Green, S.B. et al., "Influence of B2–Adrenergic Receptor Genotypes on Signal Transduction in Human Airway Smooth Muscle Cells," Am. J. Respir. Cell Mol. Biol., vol. 13, p. 25–33, (1995).
Green, S.B. et al., "Amino–Terminal Polymorphisms of the Human B2–Adrenergic Receptor Impart Distinct Agonist–Promoted Regulatory Properties," Biochemistry, vol. 33, p. 9414–9419, (1994).
Green, S.B. et al., "A Polymorphism of the Human B2–Adrenergic Receptor within the Fourth Transmembrane Domain Alters Ligand Binding and Functional Properties of hte Receptor," The Journal of Biological Chemistry, vol. 268, p. 23116–21,(1993).

Hall, Ian et al., "Association of Glu27 B2–Adrenoceptor Polymorphism with Lower Airway Reactivity in Asthmatic Subjects," The Lancet, vol. 345, p. 1213–4, (1995).
Liggett, S.B., "Functional Properties of Human B2–Adrenergic Receptor Polymorphisms," News in Physiological Sciences, vol. 10, p. 265–273, (1995).
Liggett, S.B., "The Genetics of B2–Adrenergic Receptor Polymorphisms: Relevance to Receptor Function and Asthmatic Phenotypes," The Genetics of Asthma, 1st ed., Marcel Dekker (New York), p. 455–478, (1996).
Liggett, S.B. et al., "The Ile164 B2–Adrenergic Receptor Polymorphism Adversely Affects the Outcome of Congestive Heart Failure," J. Clin. Invest., vol. 102 (No. 8), p. 1534–1539, (1998).
Liggett, S.B., "Polymorphisms in the 5' Leader Cistron of the B2–Adrenergic Receptor," Pending U.S. application Ser. No. 09/856,803, (Filed May 25, 2001).
McGraw, D.W. et al., "Polymorphisms in the 5' Leader Cistron of the Human B2–Adrenergic Receptor Regulate Receptor Expression," J. Clin. Invest., vol. 102 (No. 11), p. 1927–1932, (1998).
Reihsaus, Ellen et al., "Mutations in the Gene Encoding for the B2–Adrenergic Receptor In Normal and Asthmatic Subjects," Am. J. Respir. Cell Mol. Biol., vol. 8, p. 334–339, (1993).
Turki, Jamal et al., "*Genetic Polymorphism* of the B2–Adrenergic Receptor in Nocturnal and Nonnocturnal Asthma," J. Clin. Invest., p. 1635–1641, (1995).
Liggett, S.B., "Polymorphisms of the B2–Adrenergic Receptor and Asthma," Am. J. Respir Crit Care Med., p. 5156–5162, (1997).
Tan, Soong, et al., "Association Between B2–Adrenoceptor Polymorphisms and Susceptibility to Bronchodilator Desensitisation in Moderately Severe Stable Asthmatics," The Lancet, p. 995–999, (1997).

* cited by examiner

Primary Examiner—Gary Benzion
Assistant Examiner—Jeanine Goldberg
(74) Attorney, Agent, or Firm—Melodie W. Henderson; Matthew M. Catlett

(57) ABSTRACT

A method for predicting an individual's response to the β-agonists salmeterol, albuterol, metaproterenol, terbutaline and formoterol is disclosed. Individuals expressing the Ile164 $\beta_2$AR variant are likely to exhibit a reduced response as compared to individuals expressing the Thr164 $\beta_2$AR variant. The method is useful for making treatment decisions for patients suffering from asthma and chronic obstructive pulmonary diseases.

4 Claims, 6 Drawing Sheets

SEQUENCE LISTING

<160> NUMBER OF SEQ ID NOS: 2

<210> SEQ ID NO 1
<211> LENGTH: 413
<212> TYPE: PRT
<213> ORGANISM: Homo sapiens

<400> SEQUENCE: 1

```
Met Gly Gln Pro Gly Asn Gly Ser Ala Phe Leu Leu Ala Pro Asn Arg
  1               5                  10                  15

Ser His Ala Pro Asp His Asp Val Thr Gln Gln Arg Asp Glu Val Trp
             20                  25                  30

Val Val Gly Met Gly Ile Val Met Ser Leu Ile Val Leu Ala Ile Val
         35                  40                  45
```

```
Phe Gly Asn Val Leu Val Ile Thr Ala Ile Ala Lys Phe Glu Arg Leu
 50                  55                  60
Gln Thr Val Thr Asn Tyr Phe Ile Thr Ser Leu Ala Cys Ala Asp Leu
 65                  70                  75                  80
Val Met Gly Leu Ala Val Val Pro Phe Gly Ala Ala His Ile Leu Met
                 85                  90                  95
Lys Met Trp Thr Phe Gly Asn Phe Trp Cys Glu Phe Trp Thr Ser Ile
                100                 105                 110
Asp Val Leu Cys Val Thr Ala Ser Ile Glu Thr Leu Cys Val Ile Ala
                115                 120                 125
Val Asp Arg Tyr Phe Ala Ile Thr Ser Pro Phe Lys Tyr Gln Ser Leu
130                 135                 140
Leu Thr Lys Asn Lys Ala Arg Val Ile Ile Leu Met Val Trp Ile Val
145                 150                 155                 160
Ser Gly Leu Thr Ser Phe Leu Pro Ile Gln Met His Trp Tyr Arg Ala
                165                 170                 175
Thr His Gln Glu Ala Ile Asn Cys Tyr Ala Asn Glu Thr Cys Cys Asp
                180                 185                 190
Phe Phe Thr Asn Gln Ala Tyr Ala Ile Ala Ser Ser Ile Val Ser Phe
                195                 200                 205
Tyr Val Pro Leu Val Ile Met Val Phe Val Tyr Ser Arg Val Phe Gln
210                 215                 220
Glu Ala Lys Arg Gln Leu Gln Lys Ile Asp Lys Ser Glu Gly Arg Phe
225                 230                 235                 240
His Val Gln Asn Leu Ser Gln Val Glu Gln Asp Gly Arg Thr Gly His
                245                 250                 255
Gly Leu Arg Arg Ser Ser Lys Phe Cys Leu Lys Glu His Lys Ala Leu
                260                 265                 270
Lys Thr Leu Gly Ile Ile Met Gly Thr Phe Thr Leu Cys Trp Leu Pro
                275                 280                 285
Phe Phe Ile Val Asn Ile Val His Val Ile Gln Asp Asn Leu Ile Arg
                290                 295                 300
Lys Glu Val Tyr Ile Leu Leu Asn Trp Ile Gly Tyr Val Asn Ser Gly
305                 310                 315                 320
Phe Asn Pro Leu Ile Tyr Cys Arg Ser Pro Asp Phe Arg Ile Ala Phe
                325                 330                 335
Gln Glu Leu Leu Cys Leu Arg Arg Ser Ser Leu Lys Ala Tyr Gly Asn
                340                 345                 350
Gly Tyr Ser Ser Asn Gly Asn Thr Gly Glu Gln Ser Gly Tyr His Val
                355                 360                 365
Glu Gln Glu Lys Glu Asn Lys Leu Leu Cys Glu Asp Leu Pro Gly Thr
                370                 375                 380
Glu Asp Phe Val Gly His Gln Gly Thr Val Pro Ser Asp Asn Ile Asp
385                 390                 395                 400
Ser Gln Gly Arg Asn Cys Ser Thr Asn Asp Ser Leu Leu
                405                 410
```

<210> SEQ ID NO 2
<211> LENGTH: 413
<212> TYPE: PRT
<213> ORGANISM: Homo sapiens

<400> SEQUENCE: 2

```
Met Gly Gln Pro Gly Asn Gly Ser Ala Phe Leu Leu Ala Pro Asn Arg
  1               5                  10                  15
```

-continued

```
Ser His Ala Pro Asp His Asp Val Thr Gln Gln Arg Asp Glu Val Trp
             20                  25                  30

Val Val Gly Met Gly Ile Val Met Ser Leu Ile Val Leu Ala Ile Val
             35                  40                  45

Phe Gly Asn Val Leu Val Ile Thr Ala Ile Ala Lys Phe Glu Arg Leu
 50                      55                      60

Gln Thr Val Thr Asn Tyr Phe Ile Thr Ser Leu Ala Cys Ala Asp Leu
 65                      70                      75                  80

Val Met Gly Leu Ala Val Val Pro Phe Gly Ala His Ile Leu Met
                 85                  90                      95

Lys Met Trp Thr Phe Gly Asn Phe Trp Cys Glu Phe Trp Thr Ser Ile
             100                 105                 110

Asp Val Leu Cys Val Thr Ala Ser Ile Glu Thr Leu Cys Val Ile Ala
             115                 120                 125

Val Asp Arg Tyr Phe Ala Ile Thr Ser Pro Phe Lys Tyr Gln Ser Leu
130                     135                     140

Leu Thr Lys Asn Lys Ala Arg Val Ile Ile Leu Met Val Trp Ile Val
145                     150                     155                 160

Ser Gly Leu Ile Ser Phe Leu Pro Ile Gln Met His Trp Tyr Arg Ala
                 165                 170                 175

Thr His Gln Glu Ala Ile Asn Cys Tyr Ala Asn Glu Thr Cys Cys Asp
             180                 185                 190

Phe Phe Thr Asn Gln Ala Tyr Ala Ile Ala Ser Ser Ile Val Ser Phe
             195                 200                 205

Tyr Val Pro Leu Val Ile Met Val Phe Val Tyr Ser Arg Val Phe Gln
210                     215                     220

Glu Ala Lys Arg Gln Leu Gln Lys Ile Asp Lys Ser Glu Gly Arg Phe
225                     230                     235                 240

His Val Gln Asn Leu Ser Gln Val Glu Gln Asp Gly Arg Thr Gly His
                 245                 250                 255

Gly Leu Arg Arg Ser Ser Lys Phe Cys Leu Lys Glu His Lys Ala Leu
             260                 265                 270

Lys Thr Leu Gly Ile Ile Met Gly Thr Phe Thr Leu Cys Trp Leu Pro
             275                 280                 285

Phe Phe Ile Val Asn Ile Val His Val Ile Gln Asp Asn Leu Ile Arg
290                     295                     300

Lys Glu Val Tyr Ile Leu Leu Asn Trp Ile Gly Tyr Val Asn Ser Gly
305                     310                     315                 320

Phe Asn Pro Leu Ile Tyr Cys Arg Ser Pro Asp Phe Arg Ile Ala Phe
                 325                 330                 335

Gln Glu Leu Leu Cys Leu Arg Arg Ser Ser Leu Lys Ala Tyr Gly Asn
             340                 345                 350

Gly Tyr Ser Ser Asn Gly Asn Thr Gly Glu Gln Ser Gly Tyr His Val
             355                 360                 365

Glu Gln Glu Lys Glu Asn Lys Leu Leu Cys Glu Asp Leu Pro Gly Thr
370                     375                     380

Glu Asp Phe Val Gly His Gln Gly Thr Val Pro Ser Asp Asn Ile Asp
385                     390                     395                 400

Ser Gln Gly Arg Asn Cys Ser Thr Asn Asp Ser Leu Leu
                 405                 410
```

VARIATION IN DRUG RESPONSE RELATED TO POLYMORPHISMS IN $\beta_2$-ADRENERGIC RECEPTOR This application is a 35 U.S.C. § 371 application of PCT/US00/06502, filed Mar. 10, 2000, which claims priority to U.S. Provisional Application Ser. No. 60/124,060, filed Mar. 12, 1999.

FIELD OF THE INVENTION

This invention relates to the fields of pharmacogenomics, diagnostics and patient therapy. More specifically, the present invention relates to methods of diagnosing and/or treating diseases involving the $\beta_2$-adrenergic receptor or its isoforms.

BACKGROUND OF THE INVENTION $\beta_2$-adrenergic receptors ($\beta_2$AR) are G protein coupled receptors that are activated by endogenous catecholamines. When activated by agonists, $\beta_2$AR couple to the G proteins which then signal to effectors such as adenylyl cyclase. These receptors are widely distributed, and play important roles in regulating cardiac, vascular, pulmonary, and metabolic functions. The $\beta_2$AR expressed on cells of the lung act on the bronchial smooth muscle to relax the muscle, thus leading to bronchodilitation. Agonists acting at $\beta_2$AR (clinically referred to as $\beta$-agonists) are widely used in the treatment of asthma and chronic obstructive pulmonary diseases (COPD) such as emphysema and chronic bronchitis.

Studies of such physiologic functions of $\beta_2$AR in humans have revealed several observations. First, there appears to be substantial interindividual variation in responsiveness, and secondly receptor function appears to be dynamically regulated as indicated by intraindividual variation. Recently, significant genetic variability in the structure of the $\beta_2$AR in the human population due to single nucleotide polymorphisms (SNPs) in the $\beta_2$AR gene has been delineated (1, 2). These polymorphisms are located at nucleotides 46 (A or G), 79 (C or G), 100 (G or A) and 491 (C or T) of the coding block (where the A of the ATG start codon is designated as nucleotide position 1; GenBank Accession No. AF022956), and result in variation that occurs in the amino-terminus of the receptor at amino acids 16 (Arg or Gly), 27 (Gln or Glu) and 34 (Val or Met) and in the fourth transmembrane spanning domain at amino acid 164 (Thr or Ile). In recombinant cell studies (3, 4), and in primary cultures of cells endogenously expressing these variants (5), clear phenotypic differences have been shown between the polymorphic receptors. The Gly16 receptor was found to undergo enhanced agonist-promoted downregulation of receptor number as compared to the Arg16 receptor (3). In contrast, the Glu27 receptor was found to undergo very little agonist-promoted downregulation compared to the Gln27 receptor (3). These variants are common in the population (1). The Ile64 receptor, which occurs in the heterozygous state in ~5% of the population, displays depressed coupling to the stimulatory G protein, $G_s$ (4).

Subsequent studies have assessed the role of the aforementioned polymorphic $\beta_2$AR in diseases such as asthma [reviewed in (6)], based on the role of $\beta_2$AR in modulating bronchial smooth muscle tone. In these studies, no differences in the frequencies of any of these polymorphisms between non-asthmatics and asthmatics have been reported. However, amino acid variation at positions 16 and 27 were found to act as significant disease modifiers (7–10). In the majority of the above cited studies, the presumption has been that the clinical phenotypes of those with the Gly16 variant were due to enhanced downregulation of this receptor (as compared to those with the Arg16 receptor) by endogenous catecholamines. Thus responsiveness in individuals with this polymorphism has been considered depressed due to this tonic downregulation. A similar scenario is considered in those with the Glu27 variant, where responsiveness is greater than those with the Gln27 receptor, presumably due to its minimal downregulation by catecholamines. An amplification of these differences may occur during chronic agonist administration, as has recently been shown in asthma (11).

Previous studies (4) with the agonists epinephrine, norepinephrine, and isoproterenol have shown that the Ile164 receptor displays a small decrease in binding affinity to the receptor as determined in competition binding studies with $[^{125}I]$cyanopindolol ($[^{125}I]$cyp) in the presence of GTP. Similarly, binding curves with isoproterenol in the absence of GTP were different between the two receptors (FIG. 2). This indicates that binding of these agents at the classic agonist binding domains of the $\beta_2$AR in transmembrane segments 3 and 5 of the receptor is of lower affinity. However, they do not provide information on the binding affinities of other agonists, which have diverse structures and are commonly used to treat lung disease, or the duration of action of such agonists or interactions of such agonists to other parts of the receptor. The nature of the Ile164 receptor is further clouded by an examination of the ability of the Ile164 receptor to stimulate adenylyl cyclase compared to the more prevalent (Thr164) receptor. For example, studies show that the agonist epinephrine produces decreased stimulation while the agonist dopamine displays normal binding affinities and does not show decreased stimulation. Therefore, the effects of substituting Ile for Thr at amino acid 164 on biological activity of the $\beta_2$AR receptor in vitro or in vivo are unclear.

Salmeterol, a unique agonist used in the treatment of asthma and COPD, has been shown to interact with the human $\beta_2$AR (12). Salmeterol has a long duration of action (~12 hrs) after a single administration. The long side chain of the molecule (see FIG. 3) interacts with the receptor in a manner that tethers the molecule to the fourth transmembrane spanning domain. This region is termed the "exosite" because it is outside of the agonist binding sites of traditional agonists. Once anchored, the amine and catechol groups of the molecule, repetitively, interact with the active binding site in transmembrane domains 3 and 5. This was determined by making chimeric $\beta_2$-$\beta_1$AR mutants which allowed definition of the general area where salmeterol interacts in this unique way with the $\beta_2$AR. Studies of the interaction between salmeterol and chimeric $\beta_2$ARs having altered exosite regions indicate that salmeterol derives its increased duration of action from an interaction with the exosite region. However, in these studies, threonine was the amino acid at position 164.

Because $\beta$-agonists are the most commonly prescribed therapeutic for asthma and pharmaceutical companies continue to introduce new $\beta$-agonists to the market, it would be useful to determine the effect of polymorphisms in the human $\beta_2$AR gene on receptor response to these drugs.

SUMMARY OF THE INVENTION

The present invention is based on the surprising discoveries (1) that the $\beta$-agonists salmeterol, albuterol, metaproterenol, terbutaline and formoterol activate the Thr164 variant of $\beta_2$AR to a higher level than the Ile164 variant and (2) that the Ile 164 variant exhibits reduced exosite binding and shorter duration of action to salmeterol. It is believed that individuals expressing the Ile164 variant will exhibit reduced response to these $\beta$-agonists and, in the case of salmeterol, will also exhibit a reduced duration of response. As all these $\beta$-agonists are currently used in the treatment of patients suffering from diseases modified by the $\beta_2$AR, particularly asthma and COPD, knowledge of a patient's genotype for the polymorphic site at nucleotide +491 (+491PS) in the $\beta_2$AR gene would be useful in prescribing appropriate $\beta$-agonist therapy.

Thus, the present invention provides diagnostic methods for predicting a patient's bronchodilating response to an agonist of $\beta_2$AR. In one embodiment, the method comprises determining the patient's genotype for the +491PS, wherein a patient who has at least one thymine at this site is likely to exhibit a poor response to the agonist. In another embodiment, the method comprises assaying a sample from the patient for expression of the Ile164 $\beta_2$AR variant, wherein presence of the Ile164 $\beta_2$AR variant indicates the patient is likely to respond poorly to the agonist. In preferred embodiments of the diagnostic method, the agonist is salmeterol, albuterol, metaproterenol, terbutaline or formoterol.

DETAILED DESCRIPTION OF THE INVENTION

Figure 1:
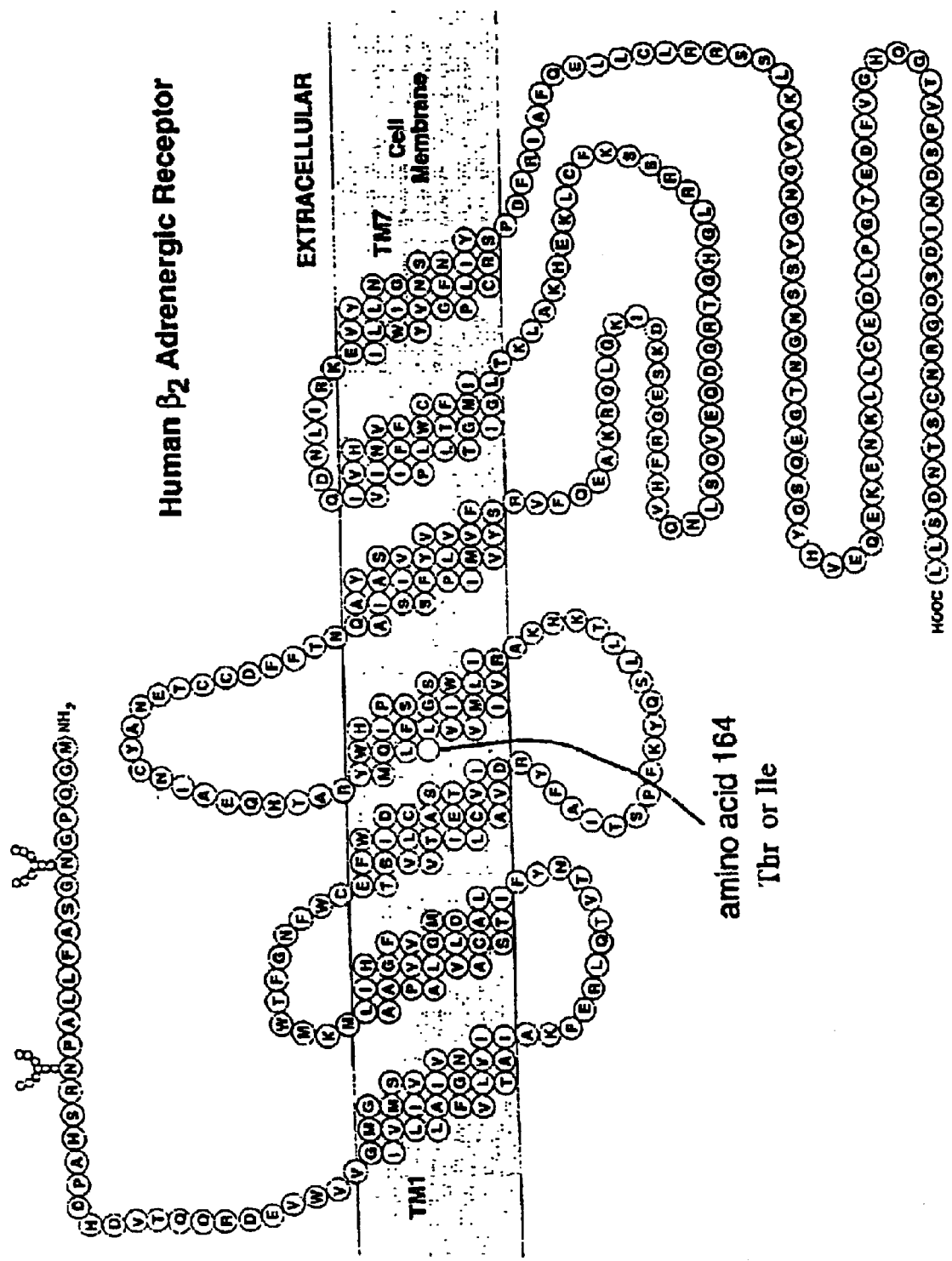
FIG. 1 illustrates a schematic of the human $\beta_2$-adrenergic receptor, with amino acid 164 shown as varying between threonine (SEQ ID NO:1) and isoleucine (SEQ ID NO:2).
Figure 2:
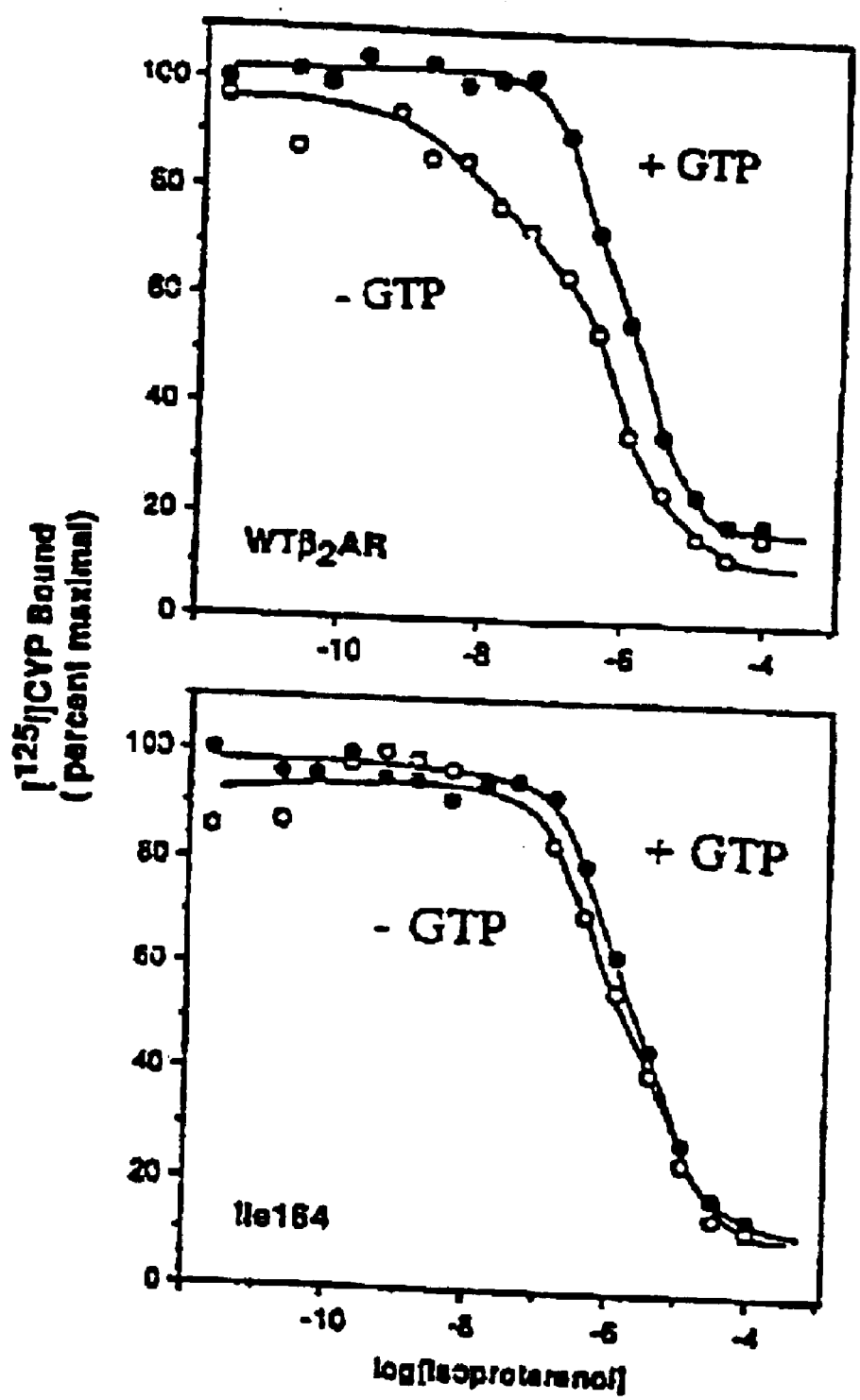
FIG. 2 is a graph comparing isoproterenol binding by the Thr164 (WT$\beta_2$AR) and Ile164 $\beta_2$AR receptors in the presence and absence of GTP.
Figure 3:
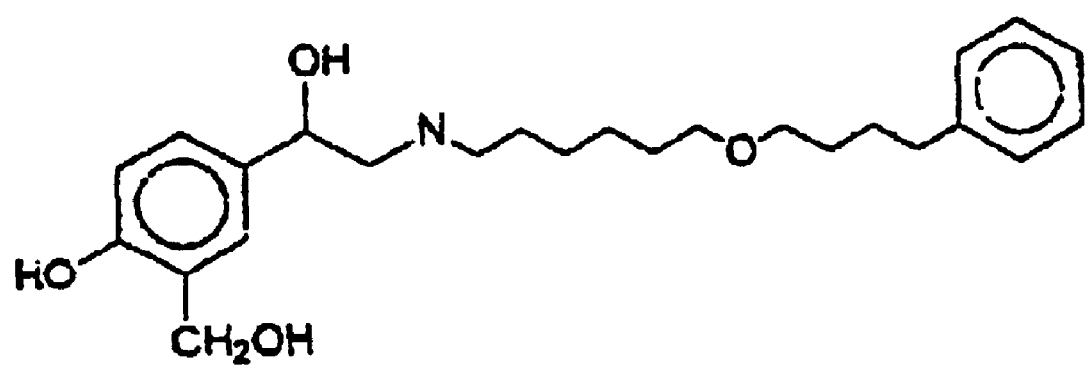
FIG. 3 illustrates the chemical structure of salmeterol.

In accordance with the present invention, the inventor herein has discovered that amino acid variation at position 164 in the $\beta_2$AR significantly affects activation of the $\beta_2$AR by $\beta$-agonists. In particular, $\beta_2$AR having isoleucine at this position are activated to a lower level than $\beta_2$AR having threonine and, in the case of salmeterol, are activated for a shorter timer period. This amino acid variation is due to a polymorphic site in the $\beta_2$AR gene that is located at nucleotide 491 of the coding block at which the two alleles are cytosine, which encodes the Thr164 variant, and thymine, which encodes the Ile164 variant. Thus, it is believed the thymine polymorphism is a marker of poor patient response to $\beta$-agonists that would be useful to a physician in making determinations as to which drug to administer, drug dosages, and duration of treatment.

In the context of this disclosure, the following terms shall be defined as follows unless otherwise indicated:

Allele—A particular form of a genetic locus, distinguished from other forms by its particular nucleotide or amino acid sequence.

Gene—A segment of DNA that contains all the information for the regulated biosynthesis of an RNA product, including promoters, exons, introns, and other untranslated regions that control expression.

Genotype—An unphased 5' to 3' sequence of nucleotide pair(s) found at one or more polymorphic sites in a locus on a pair of homologous chromosomes in an individual.

Genotyping—A process for determining a genotype of an individual.

Isoform—A particular form of a gene, mRNA, cDNA or the protein encoded thereby, distinguished from other forms by its particular sequence and/or structure.

Isolated—As applied to a biological molecule such as RNA, DNA, oligonucleotide, or protein, isolated means the molecule is for practical purposes free of other biological molecules such as non-desired nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature.

Naturally-occurring—A term used to designate that the object it is applied to, e.g., naturally-occurring polynucleotide or polypeptide, can be isolated from a source in nature and which has not been intentionally modified by man.

Nucleotide pair—The nucleotides found at a polymorphic site on corresponding strands of the two copies of a chromosome in an individual.

Polymorphic site (PS)—A position within a locus at which at least two alternative sequences are found in a population.

Polymorphic variant—A gene, mRNA, cDNA, polypeptide or peptide whose nucleotide or amino acid sequence varies from a reference sequence due to the presence of a polymorphism in the gene.

Polymorphism—The sequence variation observed in an individual at a polymorphic site. Polymorphisms include nucleotide substitutions, insertions, deletions and microsatellites and may, but need not, result in detectable differences in gene expression or protein function.

Polynucleotide—A nucleic acid molecule comprised of single-stranded RNA or DNA or comprised of complementary, double-stranded DNA.

Single Nucleotide Polymorphism (SNP)—Typically, the specific pair of nucleotides observed at a single polymorphic site. In rare cases, three or four nucleotides may be found.

In one embodiment, the invention provides a method for predicting a patient's bronchodilating response to a $\beta$-agonist, which comprises determining the patient's genotype for the +491PS. A patient who is homozygous T or heterozygous C/T at this site is likely to exhibit a poor response to the agonist. As used herein, a "poor bronchodilating response" means a reduction of about 25–50% in the improvement in FeV$_1$ typically seen after administration of the agonist to patients who are homozygous C at this position. In preferred embodiments, the agonist is selected from the group consisting of salmeterol, albuterol, metaproterenol, terbutaline and formoterol. In a particularly preferred embodiment, the agonist is salmeterol, and the patient is also likely to exhibit a decreased duration of response. As used herein, "decreased duration of response" means a reduction of about 25 to 50% in the duration of the bronchodilating response after administration of salmeterol. Thus, a patient who is heterozygous C/T or homozygous T at the +491PS would be expected to experience bronchodilation for about 6 to 9 hours instead of the approximate 12 hours typically experienced by patients who are homozygous C at this position.

The patient's genotype may be determined by isolating from the individual a nucleic acid mixture comprising the two copies of the $\beta_2AR$ gene, or a fragment thereof, that are present in the individual and determining the identity of the nucleotide pair at the +491PS in the two copies in order to assign a $\beta_2AR$ genotype to the individual. As will be readily understood by the skilled artisan, the two "copies" of a gene in an individual may be the same allele or may be different alleles. Typically, the nucleic acid mixture is isolated from a biological sample taken from the individual, such as a blood sample or tissue sample. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the $\beta_2AR$ gene is expressed. If a $\beta_2AR$ gene fragment is isolated, it must contain the +491PS and any other polymorphic sites to be genotyped.

The identity of a nucleotide pair at the +491PS may be determined by amplifying a target region containing the polymorphic site directly from both copies of the $\beta_2AR$ gene present in the individual and the sequence of the amplified region determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, since the +491PS varies between cytosine or thymine in the population, a site may be positively determined to be either cytosine or thymine for an individual homozygous at that site, or both cytosine and thymine, if the individual is heterozygous at that site. Alternatively, the site may be negatively determined to be not thymine (and thus cytosine/cytosine) or not cytosine (and thus thymine/thymine).

The target region may be amplified using any oligonucleotide-directed amplification method, including but not limited to polymerase chain reaction (PCR) (U.S. Pat. No. 4,965,188), ligase chain reaction (LCR) (Barany et al., *Proc. Natl. Acad. Sci. USA* 88:189–193, 1991; WO90/01069), and oligonucleotide ligation assay (OLA) (Landegren et al., *Science* 241:1077–1080, 1988). Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et L., *Proc. Natl. Acad. Sci. USA* 89:392–396, 1992.

Oligonucleotides useful as primers or probes in determining the $\beta_2AR$ genotype should specifically hybridize to a region of the nucleic acid that contains or is adjacent to the +491PS. As used herein, the term "oligonucleotide" refers to a polynucleotide molecule having less than about 100 nucleotides. A preferred oligonucleotide of the invention is 10 to 35 nucleotides long. More preferably, the oligonucleotide is between 15 and 30, and most preferably, between 20 and 25 nucleotides in length. The exact length of the oligonucleotide will depend on many factors that are routinely considered and practiced by the skilled artisan. The oligonucleotide may be comprised of any phosphorylation state of ribonucleotides, deoxyribonucleotides, and acyclic nucleotide derivatives, and other functionally equivalent derivatives, provided that if used as a primer, the 3' terminus of the oligonucleotide is capable of acting as a substrate for extension by a polymerase. Alternatively, oligonucleotide probes used in the may have a phosphate-free backbone, which may be comprised of linkages such as carboxymethyl, acetamidate, carbamate, polyamide (peptide nucleic acid (PNA)) and the like (Varma, R. in *Molecular Biology and Biotechnology, A Comprehensive Desk Reference*, Ed. R. Meyers, VCH Publishers, Inc. (1995), pages 617–620). Oligonucleotides used for genotyping may be prepared by chemical synthesis using any suitable methodology known in the art, or may be derived from a biological sample, for example, by restriction digestion. The oligonucleotides may be labeled, according to any technique known in the art, including the use of radiolabels, fluorescent labels, enzymatic labels, proteins, haptens, antibodies, sequence tags and the like.

Oligonucleotide probes and primers useful in the invention must be capable of specifically hybridizing to a target region in the isolated nucleic acid that contains the +491PS. As used herein, specific hybridization means the oligonucleotide reacts with the target region with sufficient specificity to allow the skilled artisan to discriminate between hybridization to the target region and hybridization to a non-target region. Preferably, the oligonucleotide specifically hybridizes to the target region under conventional high stringency conditions. The skilled artisan can readily design and test oligonucleotide probes and primers suitable for detecting the $\beta_2AR$ +491PS using the information provided herein in conjunction with the known sequence information for the $\beta_2AR$ gene and routine techniques.

In describing the $\beta_2AR$ +491 polymorphic site identified herein, reference is made to the sense strand of the gene for convenience. However, as recognized by the skilled artisan, nucleic acid molecules containing the $\beta_2AR$ gene may be complementary double stranded molecules and thus reference to a particular site on the sense strand refers as well to the corresponding site on the complementary antisense strand. Thus, reference may be made to either strand and still comprise the same polymorphic site and an oligonucleotide may be designed to specifically hybridize to either strand.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, by Sambrook J. et al., in *Molecular Cloning, A Laboratory Manual*, $2^{nd}$ Edition, Cold Spring Harbor Press, Cold Spring Harbor, N.Y. (1989) and by Haymes, B. D. et al. in *Nucleic Acid Hybridization, A Practical Approach*, IRL Press, Washington, D.C. (1985). While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the oligonucleotide probe or primer as long as the resulting probe or primer is still capable of specifically hybridizing to the target region.

The +491PS may also be assayed before or after amplification using one of several hybridization-based methods known in the art. Typically, allele-specific oligonucleotides are utilized in performing such methods. As used herein, the term allele-specific oligonucleotide (ASO) means an oligonucleotide that is able, under sufficiently stringent conditions, to specifically hybridize to one allele of the $\beta_2$AR gene at a target region containing the +491 polymorphic site while not hybridizing to the corresponding region in the other allele. As understood by the skilled artisan, allele-specificity will depend upon a variety of readily optimized stringency conditions, including salt and formamide concentrations, as well as temperatures for both the hybridization and washing steps. Examples of hybridization and washing conditions typically used for ASO probes are found in Kogan et al., "Genetic Prediction of Hemophilia A" in *PCR Protocols, A Guide to Methods and Applications*, Academic Press, 1990 and Ruano et al., 87 *Proc. Natl. Acad. Sci. USA* 6296–6300, 1990. Typically, an ASO will be perfectly complementary to one allele while containing a single mismatch for another allele.

Allele-specific oligonucleotide probes which usually provide good discrimination between different alleles are those in which a central position of the oligonucleotide probe aligns with the polymorphic site in the target region (e.g., approximately the $7^{th}$ or $8^{th}$ position in a 15 mer, the $8^{th}$ or $9^{th}$ position in a 16 mer, the $10^{th}$ or $11^{th}$ position in a 20 mer). An allele-specific oligonucleotide primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. Allele-specific oligonucleotide primers hybridizing to either the coding or noncoding strand are contemplated by the invention.

The allele-specific oligonucleotides may be used as differently labeled probe pairs, with one member of the pair showing a perfect match to one variant of the target sequence and the other member showing a perfect match to the other variant. Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype for one or more polymorphic sites in the $\beta_2$AR gene of an individual may also be determined by hybridization of both copies of the gene, or a fragment thereof, to nucleic acid arrays and subarrays such as described in WO 95/11995. The arrays would contain a battery of allele-specific oligonucleotides representing each of the polymorphic sites to be included in the genotype.

The identity of the nucleotide pair at the +491PS may also be determined using a mismatch detection technique, including but not limited to the RNase protection method using riboprobes (Winter et al., *Proc. Natl. Acad. Sci. USA* 82:7575, 1985; Meyers et al., *Science* 230:1242, 1985) and proteins which recognize nucleotide mismatches, such as the *E. coli* mutS protein (Modrich, P. *Ann. Rev. Genet.* 25:229–253 (1991). Alternatively, the variant alleles can be identified by single strand conformation polymorphism (SSCP) analysis (Orita et al., *Genomics* 5:874–879, 1989; Humphries et al., in *Molecular Diagnosis of Genetic Diseases*, R. Elles, ed., pp 321–340, 1996) or denaturing gradient gel electrophoresis (DGGE) (Wartell et al., *Nucl. Acids Res.* 18:2699–2706, 1990; Sheffield et al., *Proc. Natl. Acad Sci. USA* 86:232–236, 1989).

A polymerase-mediated primer extension method may also be used to identify the polymorphism at the +491PS. Several such methods have been described in the patent and scientific literature and include the "Genetic Bit Analysis" method (WO92/15712) and the ligase/polymerase mediated genetic bit analysis (U.S. Pat. No. 5,679,524. Related methods are disclosed in WO91/02087, WO90/09455, WO95/17676, and U.S. Pat. No. 5,302,509. Another such method is allele-specific PCR (Ruano et al., *Nucl. Acids Res.* 17:8392, 1989; Ruano et al., *Nucl. Acids Res.* 19, 6877–6882, 1991; WO 93/22456; Turki et al., *J. Clin. Invest.* 95:1635–1641, 1995).

Another aspect of the invention relates to detecting expression of the Ile164 $\beta_2$AR variant in a biological sample from an individual. In one embodiment, the biological sample is contacted with a first antibody that is specifically immunoreactive with the Ile164 $\beta_2$AR variant, i.e., it does not react with the Thr164 $\beta_2$AR variant, and the formation of a complex with the first antibody is detected. Complex formation indicates the individual expresses the Ile164 $\beta_2$AR variant and thus is likely to exhibit a poor response to a $\beta$-agonist. In a preferred embodiment, the method also comprises contacting the biological sample with a second antibody that is specifically immunoreactive with the Thr164 $\beta_2$AR variant and the formation of a complex with the second antibody is detected. Complex formation with both first and second antibodies indicate the individual expresses both variants.

Suitable immunoassays for use in this detection method include radioimmunoassay, Western blot assay, immunofluorescent assay, enzyme linked immunoassay (ELISA), chemiluminescent assay, immunohistochemical assay, immunocytochemical assay, and the like (see, e.g., *Principles and Practice of Immunoassay*, 1991, Eds. Christopher P. Price and David J. Neoman, Stockton Press, New York, N.Y.; *Current Protocols in Molecular Biology*, 1987, Eds. Ausubel et al., John Wiley and Sons, New York, N.Y.). Standard techniques known in the art for ELISA are described in *Methods in Immunodiagnosis*, 2nd Ed., Eds. Rose and Bigazzi, John Wiley and Sons, New York 1980; and Campbell et al., 1984, *Methods in Immunology*, W. A. Benjamin, Inc.). Such assays may be direct, indirect, competitive, or noncompetitive as described in the art (see, e.g., *Principles and Practice of Immunoassay*, 1991, Eds. Christopher P. Price and David J. Neoman, Stockton Press, NY, N.Y.; and Oellirich, M., 1984, *J. Clin. Chem. Clin. Biochem.*, 22:895–904). Proteins may be isolated from test specimens and biological samples by conventional methods, as described in *Current Protocols in Molecular Biology*, supra.

Exemplary antibody molecules for detecting the Ile164 and Thr164 $\beta_2AR$ variants are intact immunoglobulin molecules, substantially intact immunoglobulin molecules, or those portions of immunoglobulin molecules that contain the antigen binding site. Polyclonal or monoclonal antibodies may be produced by methods conventionally known in the art (e.g., Kohler and Milstein, 1975, *Nature*, 256:495–497; Campbell "Monoclonal Antibody Technology, the Production and Characterization of Rodent and Human Hybridomas", 1985, In: "Laboratory Techniques in Biochemistry and Molecular Biology," Eds. Burdon et al., Volume 13, Elsevier Science Publishers, Amsterdam). The antibodies or antigen binding fragments thereof may also be produced by genetic engineering. The technology for expression of both heavy and light chain genes in *E. coli* is the subject of PCT patent applications, publication number WO 901443, WO 901443 and WO 9014424 and in Huse et al., 1989, *Science*, 246:1275–1281. The antibodies may also be humanized (e.g., Queen, C. et al. 1989 *Proc. Natl. Acad. Sci.* 86;10029).

EXAMPLES

The Examples herein are meant to exemplify the various aspects of carrying out the invention and are not intended to limit the scope of the invention in any way. The Examples do not include detailed descriptions for conventional methods employed, such as in the synthesis of oligonucleotides or preparation of antibodies. Such methods are well known to those skilled in the art and are described in numerous publication's, for example, Sambrook, Fritsch, and Maniatis, *Molecular Cloning: a Laboratory Manual*, 2$^{nd}$ Edition, Cold Spring Harbor Laboratory Press, USA, (1989).

Example 1

This example illustrates the effect of the amino acid variation at position 164 in the $\beta_2AR$ on exosite binding of salmeterol.

The exosite binding studies were carried out by methods as described in reference 4. Briefly, COS-7 cells were transiently transfected with constructs consisting of Thr164 or Ile164 cDNAs in the vector pBC12BI as previously described (4). Cells were grown in 35 mm dishes as monolayers. Two days after transfection, cells were treated with media alone (control) or media with salmeterol for 10 minutes at 37° C. The media was removed, and cells perfused with saline at a rate of 20 ml/min for 30 min. Cells were detached by scraping and cell membranes prepared. [$^{125}$I]CYP binding was carried out by incubating membranes, in triplicate, with 400 pM [$^{125}$I]CYP in the absence (total binding) and presence (non-specific binding) of 1 $\mu$M propranolol. Reactions were run for 2 hrs at 25° C. Bound radioligand was separated from unbound by vacuum filtration over Whatman GF/C filters, which were counted in a gamma counter at 70% efficiency. Specific binding was defined as total minus non-specific binding, corrected for protein. If salmeterol tightly binds to a given receptor, despite the washout, then there are few sites available for [$^{125}$I]CYP binding. Exosite binding, then, was defined as:

$$[[^{125}I]CYP \text{ binding control}-[^{125}I]CYP \text{ binding salmeterol}]\times 100\%$$

Figure 4:
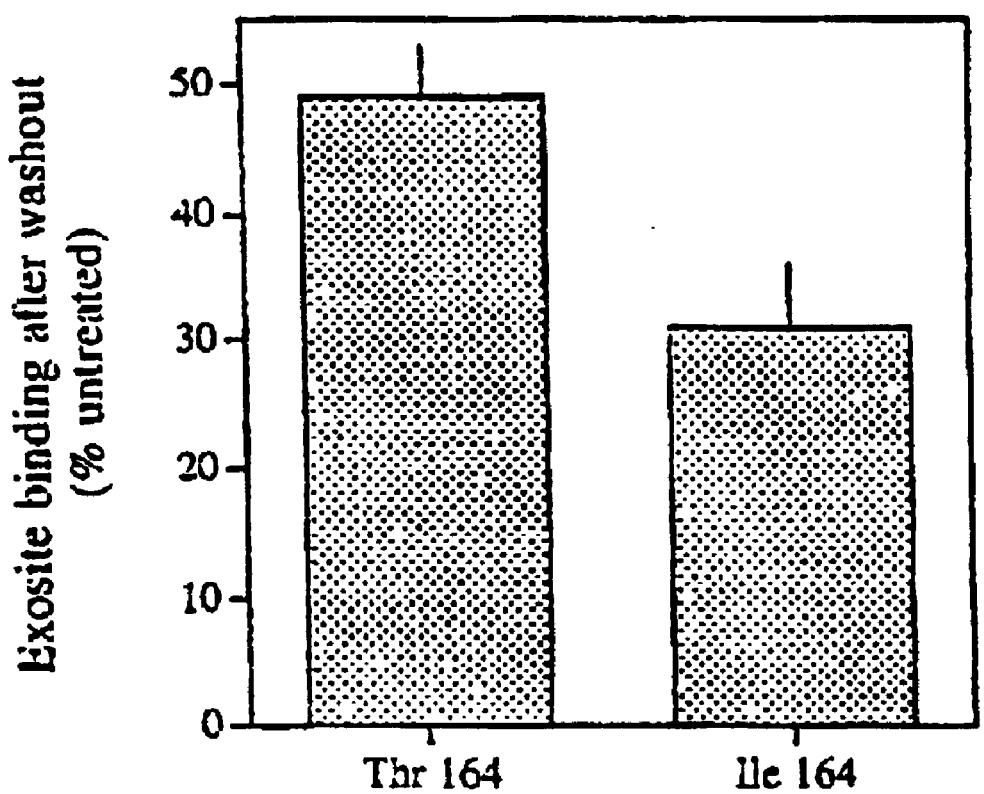
FIG. 4 illustrates a bar graph comparing exosite binding between the Thr164 and Ile164 receptors.

The results are shown in FIG. 4. The Ile164 receptor clearly has less salmeterol exosite binding compared to the Thr164 receptor (31±5 verses 49±4%, n=5, p=0.02). This finding could not have been predicted from previous traditional agonist competition binding studies, which measure the ability of the agonist to interact with the receptor at the active sites in transmembrane regions 3 and 5, but not to sites that act to tether a side chain of the agonist to a region of the receptor. In addition, traditional competition studies such as these are carried out in washed membranes from cells not previously exposed to an agonist. There is no way in these types of assays that the agonist can interact with the receptor as it does when expressed in living cells. In contrast, the exosite binding experiments used in making the present invention utilize agonist exposure to living cells expressing $\beta_2AR$ in culture which are then washed extensively and the number of receptors that remain bound by agonist is assessed by radioligand binding to cell membranes.

Example 2

This example illustrates the effect of amino acid variation at position 164 on salmeterol-induced activation of the $\beta_2AR$.

cAMP functional studies were performed to confirm the exosite binding results described in Example 1. cAMP is quantitated to give a measure of functional activity after washout, which should be higher if more agonist is being retained at the receptor. In these studies, which were carried out as previously described (12), cAMP levels were measured in supernatants from Chinese hamster fibroblast cells expressing the two receptors that had been treated and washed as above. If salmeterol remains bound despite washout, cAMP generation would be elevated because the receptor is being activated by an agonist. Data is reported from these studies as the percent cAMP levels compared to the control response to salmeterol without washout. cAMP levels were quantitated using a radioimmunoassay as described (12).

Figure 5:
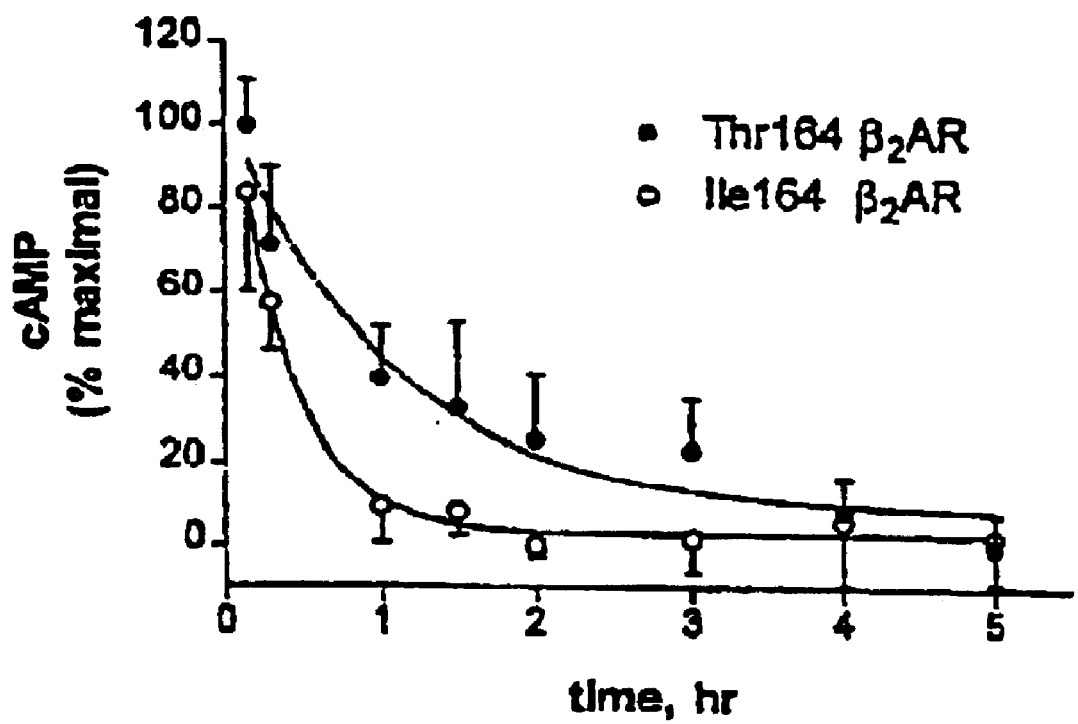
FIG. 5 illustrates a graph comparing the amount and duration of response of the Thr164 and Ile164 receptors to salmeterol.

As shown in FIG. 5, following washing, the Ile164 receptor had a loss of cAMP response with a half-time of 0.35±0.06 hours compared to 0.78±0.06 hours for the Thr164 receptor (p=0.001, n=5). This represents an approximately 50% decrease in duration of action.

Example 3

This example illustrates the effect of amino acid variation at position 164 on the amount of activation of the $\beta_2AR$ by several $\beta$-agonists.

Figure 6:
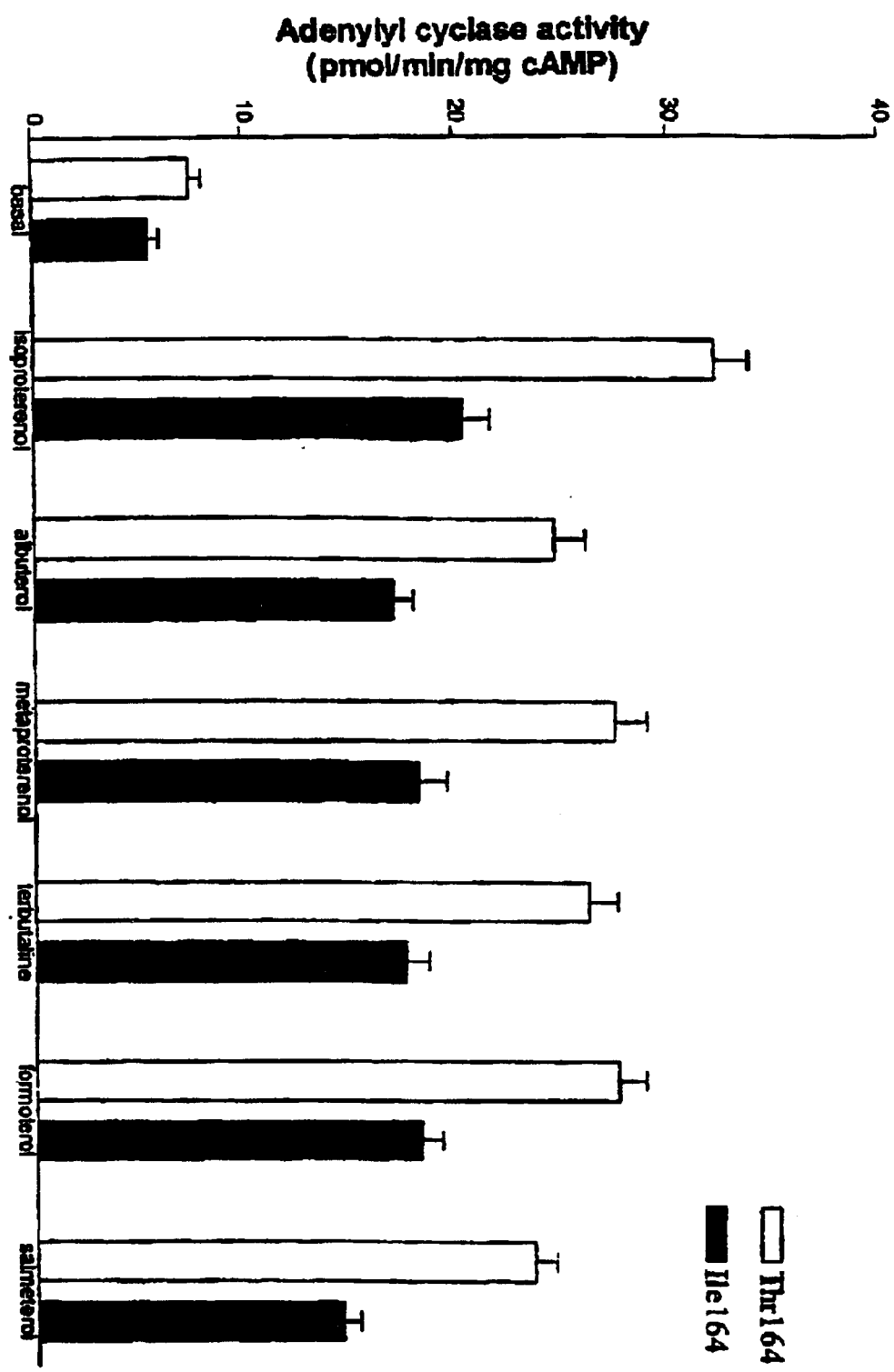
FIG. 6 illustrates a graph comparing the amount of activation of the Thr164 and Ile164 receptors by various $\beta$ agonists.

The ability of the $\beta$-agonists albuterol, metaproterenol, terbutaline, formoterol and salmeterol to activate the $\beta_2AR$ recombinantly expressed in CHW-1102 cells was examined. These studies were carried out in cell membranes by examining the stimulation of the enzyme adenylyl cyclase, which is the dominant effector for $\beta_2AR$, and the results are shown in FIG. 6.

Salmeterol, albuterol, metaproterenol, terbutaline and formoterol failed to stimulate adenylyl cyclase in the cells expressing the Ile164 variant to the same extent as in the cells expressing the Thr164 variant. Thus, not withstanding duration of action, salmeterol, albuterol, metaproterenol, terbutaline and formoterol will have a depressed acute response in individuals expressing the Ile164 $\beta_2AR$.

In conclusion, use of $\beta$-agonists in the treatment of asthma and COPD can be improved by use of the diagnostic methods of the present invention. As indicated, the thymine polymorphism at the +491PS alters the response of the $\beta_2AR$ to salmeterol, albuterol, metaproterenol, terbutaline and formoterol. Individuals homozygous or heterozygous for this allele are expected to respond worse to drug treatment than those homozygous for the cytosine allele, with the latter requiring lower doses, less frequently and the former more doses more frequently.

In addition, individuals with asthma or COPD who are being treated with salmeterol and who have the thymine polymorphism will also have a considerably shorter duration of action of the drug. The duration of action of salmeterol on the Ile164 variant appears to be about 50% shorter (based on half times) than on the Thr164 receptor. Therefore, bronchodilation (and protection against bronchoconstriction) in those patients expressing the Ile164 receptor will be shorter than the 12 hours after dosing that is typically observed for patients expressing the Thr164 receptor, perhaps on the order of about 6 hours. Thus, there is a reduction in efficacy of β-agonist therapy for such individuals and the physician may wish to consider altered or alternative therapy.

In view of the above, it will be seen that the several advantages of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

All references cited in this specification, including patents and patent applications, are hereby incorporated in their entirety by reference. The discussion of references herein is intended merely to summarize the assertions made by their authors and no admission is made that any reference constitutes prior art. Applicants reserve the right to challenge the accuracy and pertinency of the cited references.

REFERENCES

1. Reihsaus, E., M. Innis, N. MacIntyre, and S. B. Liggett. 1993. Mutations in the gene encoding for the $\beta_2$-adrenergic receptor in normal and asthmatic subjects. *Am J Resp Cell Mol Biol* 8:334–339.
2. Liggett, S. B. 199S. Functional properties of human $\beta_2$-adrenergic receptor polymorphisms. News in Physiologic Sciences 10:265–273.
3. Green, S., J. Turki, M. Innis, and S. B. Liggett. 1994. Amino-terminal polymorphisms of the human $\beta_2$-adrenergic receptor impart distinct agonist-promoted regulatory properties. *Biochem* 33:9414–9419.
4. Green, S. A., G. Cole, M. Jacinto, M. Innis, and S. B. Liggett. 1993. A polymorphism of the human $\beta_2$-adrenergic receptor within the fourth transmembrane domain alters ligand binding and functional properties of the receptor. *J Biol Chem* 268:23116–23121.
5. Green, S. A., J. Turki, P. Bejarano, I. P. Hall, and S. B. Liggett. 1995. Influence of $\beta_2$-adrenergic receptor genotypes on signal transduction in human airway smooth muscle cells. *Am J Resp Cell Mol Biol* 13:25–33.
6. Liggett, S. B. 1996. The genetics of $\beta_2$-adrenergic receptor polymorphisms: relevance to receptor function and asthmatic phenotypes. In The Genetics of Asthma. S. B. Liggett and D. A. Meyers, editors. Marcel Dekker, New York. 455–478.
7. Turki, J., J. Pak, S. Green, R. Martin, and S. B. Liggett. 199S. Genetic polymorphisms of the $\beta_2$-adrenergic receptor in nocturnal and non-nocturnal asthma: evidence that Gly16 correlates with the nocturnal phenotype. *J Clin Invest* 95:1635–1641.
8. Hall, I. P., A. Wheatley, P. Wilding, and S. B. Liggett. 1995. Association of the Glu27 $\beta_2$-adrenoceptor polymorphism with lower airway reactivity in asthmatic subjects. *Lancet* 345:1213–1214.
9. Martinez, F. D., P. E. Graves, M. Baldini, S. Solomon, and R. Erickson. 1997. Association between genetic polymorphisms of the beta2-adrenoceptor and response to albuterol in children with and without a history of wheezing. *J Clin Invest* 100:3184–3188.
10. Dewar, J. C., J. Wilkinson, A. Wheatley, N. S. Thomas, I. Doull, N. Morton, P. Lio, J. Harvey, S. B. Liggett, I. S. Holgate, and I. P. Hall. 1997. The glutumine 27 $\beta_2$-adrenoceptor polymorphism is associated with elevated immunoglobulin E levels in asthmatic families. *J Allergy Clin Immunol* 100:261–265.
11. Tan, S., I. P. Hall, J. Dewar, E. Dow, and B. Lipworth. 1997. Association between beta 2-adrenoceptor polymorphism and susceptibility to bronchodilator desensitization in moderately severe stable asthmatics. *Lancet* 350:995–999.
12. Green, S. A., A. P. Spasoff, R. A. Coleman, M. Johnson, and S. B. Liggett. 1996. Sustained activation of a G protein coupled receptor via "anchored" agonist binding: Molecular localization of the salmeterol exosite within the $\beta_2$-adrenergic receptor. *J. Biol. Chem.* 271:24029–24035.

It is claimed:

1. A method for predicting an individual's bronchodilating response to an agonist of $\beta_2$AR, which comprises determining the individual's genotype for the +491PS, wherein a heterozygous C/T genotype or a homozygous T/T genotype indicates the individual is likely to exhibit a poor bronchodilating response to the agonist, wherein the agonist is selected from the group consisting of salmeterol, albuterol, metaproterenol, terbutaline and formoterol.

2. The method of claim 1, wherein the agonist is salmeterol.

3. The method of claim 2, wherein the individual suffers from asthma or COPD.

4. The method of claim 1, wherein determining the individual's genotype comprises isolating from the individual a nucleic acid mixture comprising the two copies of the $\beta_2$AR gene, or a fragment thereof, that are present in the individual and determining the identity of the nucleotide pair at +491PS in the two copies in order to assign a $\beta_2$AR genotype to the individual.

* * * * *